United States Patent [19]

Fujishima et al.

[11] Patent Number: 4,713,334

[45] Date of Patent: Dec. 15, 1987

[54] PROCESS FOR THE SACCHARIFICATION OF CELLULOSES

[75] Inventors: Shizu Fujishima, Ikeda; Fumiko Yaku, Suita; Tetsuo Koshijima, Kyoto, all of Japan

[73] Assignee: Agency of Industrial Science and Technology, Tokyo, Japan

[21] Appl. No.: 843,809

[22] Filed: Mar. 27, 1986

Related U.S. Application Data

[63] Continuation of Ser. No. 586,948, Mar. 7, 1984, abandoned.

[30] Foreign Application Priority Data

Mar. 18, 1983 [JP] Japan ................................. 58-46707
May 20, 1983 [JP] Japan ................................. 58-89480

[51] Int. Cl.$^4$ ........................ C12P 19/14; C12P 7/14; C12N 9/42
[52] U.S. Cl. ........................... 435/99; 435/162; 435/209; 435/813
[58] Field of Search ................... 435/99, 209, 162, 813

[56] References Cited

U.S. PATENT DOCUMENTS

4,220,721  9/1980  Emert et al. ..................... 435/99 X
4,487,831  12/1984 Day et al. ........................... 435/99

OTHER PUBLICATIONS

Sinitsyn et al., in Biotechnology and Bioengineering XXV, No. 5, May 1983, pp. 1393-1399.
Enzyme Engineering 7 (Annals of the New York Academy of Sciences), vol. 434, 1984, pp. 155-157.
Sinitsyn et al., in Applied Biochemistry and Biotechnology, vol. 8, pp. 25-29 (Feb. 1983).

*Primary Examiner*—Lionel M. Shapiro
*Attorney, Agent, or Firm*—Armstrong, Nikaido, Marmelstein & Kubovcik

[57] ABSTRACT

A process for the saccharification of celluloses is provided. More particularly, a solution obtained after the degradative saccharification of cellulosic materials with cellulases is separated into a liquid portion containing saccharides and a solid matter. Cellulases are recovered from said liquid portion containing saccharides, while said solid matter is treated with an aqueous pH-buffered solution, or an aqueous solution, alcoholic aqueous solution or aqueous pH-buffered solution of polysaccharides or oligosaccharides, or aqueous or aqueous pH-buffered solution of alcohols to recover the cellulases in the solid matter. With the use of this solid matter, newly added cellulosic materials are degradatively saccharified in an aqueous solution or the above-mentioned solutions.

6 Claims, No Drawings

PROCESS FOR THE SACCHARIFICATION OF CELLULOSES

This application is a continuation of application Ser. No. 586,948 filed Mar. 7, 1984, now abandoned.

BACKGROUND OF THE INVENTION

The present invention is related to a process for the saccharification of celluloses, particularly to a process for the recovery of cellulases, such as hemicellulase or cellulase from the reaction mixture obtained after the degradative saccharification (hereinafter referred to as degradative saccharification liquor) of cellulosic materials with said cellulases by remarkably simple operations in high yields, and a process for the saccharification of new cellulosic materials, making use of the enzymes adhering to the solid matter which remains in the reaction mixture after the saccharification.

Saccharification of cellulosic materials has been intensively studied recently from the viewpoints of energy saving, environmental pollution, or utilization of unexploited resources, among which enzymatic saccharification is attracting public attention as an effective process, in which cellulosic materials are saccharified with simple devices and operations, under moderate conditions, without further decomposition of the produced saccharides.

In this enzymatic saccharification, the cost for the production of cellulases used as enzyme, for example cellulase or hemicellulase, is generally accepted to account for a half of the total cost. It is very important, therefore, to recover these expensive enzymes for re-utilization. A variety of methods have been suggested for the recovery of the cellulases remaining in the degradative saccharification liquor of cellulosic materials after a liquid portion is separated from the solution by centrifugation or other processes. However, there have been no suggestions at all relating to a method of recovering the cellulases which remains in the separated solid matter, and therefore cellulases have been recovered in an amount of at most 35 to 45 percent in conventional enzymatic saccharification of cellulosic materials.

Meanwhile, the present inventors have succeeded in determining the amount of the cellulases remaining in the solid matter separated from the degradative saccharification liquor of cellulosic materials using a spectropolarimeter with the finding that the amount of the cellulases remaining in this solid matter is higher than that of the cellulases remaining in the liquid portion separated from said degradative saccharification liquor, and that more than a half of the expensive cellulases have been discarded together with the solid matter in conventional enzymatic saccharification methods. It was also understood from the results of the studies of the present inventors that the activity of the cellulases remaining in said solid matter is maintained substantially completely as in the case of the cellulases remaining in said liquid portion.

SUMMARY OF THE INVENTION

A first object of the present invention is to provide a process for the enzymatic saccharification of cellulosic materials, wherein cellulose is economically saccharified by the recovery and re-utilization of expensive enzymes.

A second object of the present invention is to provide a process for the recovery of cellulases, such as hemicellulase or cellulase from the degradative saccharification liquor of cellulosic materials with said cellulases by a simple operation in such high yields that have not been attained by conventional methods.

A third object of the present invention is to provide a process for effecting degradative saccharification of new cellulosic materials using a solid matter remaining in the degradative saccharification liquor of cellulosic materials as an enzyme substitute.

These objects of the present invention are attained by degradatively saccharifying cellulosic materials with cellulases, separating a solution obtained after the degradative saccharification into a liquid portion containing saccharides and a solid matter, recovering cellulases from said liquid portion, and recovering cellulases also from said solid matter by treating the solid matter with an aqueous solution, alcoholic aqueous solution, or aqueous pH-buffered solution of polysaccharides or oligosaccharides, or an aqueous or aqueous pH-buffered solution of alcohols, or an aqueous pH-buffered solution.

The objects of the present invention are attained also by degradatively saccharifying cellulosic materials with cellulases, separating a solution obtained after the degradative saccharification into a liquid portion containing saccharides and a solid matter, and degradatively saccharifying newly supplied cellulosic materials using said solid matter in an aqueous solution or an aqueous pH-buffered solution, or an aqueous solution, aqueous alcoholic solution or aqueous pH-buffered solution of polysaccharides or oligosaccharides, or an aqueous or aqueous pH-buffered solution of alcohols.

DETAILED DESCRIPTION OF THE INVENTION

In the present invention, first of all, a cellulosic material is degradatively saccharified with cellulases. The conditions for this degradative saccharification are not particularly limited. The cellulosic material can be degradatively saccharified according to conventional methods in, for example an aqueous solution or an aqueous pH-buffered solution, or an aqueous solution, alcoholic aqueous solution or aqueous pH-buffered solution of polysaccharides or oligosaccharides, or an aqueous or aqueous pH-buffered solution of alcohols.

The cellulosic materials used in the present invention include all the wooden materials such as small chips, sawdust, bark, or waste wood obtained from softwood or hardwood, Southeast Asian or North American timbers or their mixtures, and so on, agricultural waste which is costly in its disposal, such as rice straw, sugar cane, or corn, or newspaper, corrugated board, and other papers. Water-insoluble polysaccharides and oligosaccharides susceptible to enzymatic action as is cellulose, can also be used. These cellulosic materials are all insoluble in water.

The enzymes used in the present invention, namely cellulases, include those containing cellulase alone or together with hemicellulase produced from fungi belonging to genus Aspergillus or Trichoderma. In the present invention, these enzymes of different origins may be used by itself or in combination of two or more of them. The extract or culture solutions of the fungi containing these enzymes can also be employed as enzyme source.

According to the process of the present invention, the obtained degradative saccharification liquor is separated centrifugally or by other means into a liquid portion containing saccharides and a solid matter. The cellulases contained in the liquid portion are recovered by ultrafiltration or other ordinary methods. The recovery of the cellulases from the liquid portion is 90 to 100 percent based on the amount of the residual cellulases in the liquid.

It is essential in the present invention to recover the cellulases remaining in the separated solid matter with an aqueous solution, alcoholic aqueous solution or aqueous pH-buffered solution of water-soluble polysaccharides or oligosaccharides, or an aqueous or aqueous pH-buffered solution of alcohols, or an aqueous pH-buffered solution.

More particularly, in the present invention, the cellulases remaining in the solid matter separated from the degradative saccharification liquor are recovered either by filtering after washing the solid matter with an aqueous pH-buffered solution, or an aqueous solution, alcoholic aqueous solution or aqueous pH-buffered solution of polysaccharides or oligosaccharides, or an aqueous or aqueous pH-buffered solution of alcohols, or by adding the solid matter to said solution, and moderately stirring or shaking the mixture at a temperature ranging from 5° C. to 55° C. so that said solid matter contacts with said solution.

The water-soluble polysaccharides used for the recovery of cellulases include glucomannan, xylan, galactan, galactoglucomannan, or mixtures thereof. The oligosaccharides include cellobiose, cellotriose, cellotetraose, cellopentaose, cellohexaose, glucose-containing mannooligosaccharides, or mixtures thereof.

As the alcohol, monohydric alcohols such as ethanol or polyhydric alcohols such as ethylene glycol are used.

The pH-buffered solutions are those in which acidic buffering agents are used, such as acetate buffer, phosphate buffer, citrate buffer, or Tris buffer solution.

The concentration of the aqueous solution, alcoholic aqueous solution, or aqueous pH-buffered solution of the polysaccharides or oligosaccharides is preferably within the range of 0.5 to 5 percent by weight. When the concentration is lower than 0.5 percent by weight, the cellulases are not sufficiently recovered. On the other hand, the maximum concentration is 5 percent by weight, as it is the solubility of the water-soluble polysaccharides or oligosaccharides.

The alcohol concentration of the aqueous or aqueous pH-buffered solution of alcohols is within the range of 1 to 30 percent by volume. When the concentration is below 1 percent by volume, the cellulases are not sufficiently recovered, while in a solution containing 30 percent by volume or more of the alcohol, cellulases are susceptible to denaturation. The alcohol concentration of the alcoholic aqueous solution of polysaccharides or oligosaccharides, and of the aqueous pH-buffered solution of alcohols is within the range of 1 to 30 percent by volume based on the same reasons as above. The aqueous pH-buffered solution is used in recovery from solid matter and the degradative saccharification of new cellulosic materials with solid matter, and when it is used with polysaccharides or oligosaccharides or alcohols gives higher stability to the recovered cellulases. Its pH value is preferably within the range of 3.0 to 8.0. The solution containing cellulases recovered with the use of the aqueous solution, alcoholic aqueous solution, or aqueous pH-buffered solution of these saccharides is employed as it is as enzyme solution for the decomposition of polysaccharides or oligosaccharides, and further re-utilized as enzyme source for the degradative saccharification of cellulosic materials.

In the next step of the present invention, the solid matter separated from the reaction mixture obtained after the degradative saccharification of cellulose is employed as enzyme substitute to saccharify cellulose degradatively by contacting said solid matter with the cellulose newly supplied in an aqueous solution or an aqueous pH-buffered solution, or an aqueous solution, alcoholic aqueous solution or aqueous pH-buffered solution of polysaccharides or oligosaccharides, or an aqueous or aqueous pH-buffered solution of alcohols. Said aqueous solution, alcoholic aqueous solution, or aqueous pH-buffered solution of polysaccharides or oligosaccharides and an aqueous or aqueous pH-buffered solution of alcohols, or an aqueous pH-buffered solution are under the same conditions as described above. Of course, as mentioned above, the solution containing the recovered cellulases obtained by the treatment of the solid matter can be used for the degradative saccharification of the cellulose newly supplied, or the residual liquor obtained by the separation of saccharides alone from the degradative saccharification liquor can be contacted without being separated into a solid matter and a liquid portion with the newly supplied insoluble cellulose, so that the enzymes remaining both in the liquid portion and in the solid matter are simultaneously re-used, if a more simplified operation is desired. The solid matter is contacted with the insoluble cellulose in said solutions or pH-buffered solutions at a temperature ranging from room temperature to 55° C. If the contact is effected at a temperature lower than room temperature, the reaction is retarded. Temperatures higher than 55° C. are not desirable either because cellulases are deactivated.

In this remarkably simplified operation, the enzymes contained in the solid matter migrate to the insoluble cellulose in the newly supplied material by the affinity of the enzyme for cellulose. The activity of the cellulases remaining in the solid matter is thus re-utilized by 65 to 100 percent. After the degradative saccharification reaction is completed, the solid matter is separated from the reaction mixture in the manner described above to be utilized for the additional degradative saccharification of cellulose supplied anew. The steps of the operation are repeated in this way.

As understood from the foregoing, cellulases are recovered in a yield of as high as 75 to 100 percent by recovering cellulases from each of the liquid portion and the solid matter separated from the degradative saccharification liquor of cellulosic materials. The recovery of the cellulases according to the present invention is approximately 30 to 55 percent higher than that of the cellulases obtained by the conventional method of recovering cellulases only from the liquid portion.

The activity of the cellulases recovered according to the present invention is nothing lower than that of the cellulases conventionally recovered. These recovered cellulases can be re-utilized in the degradative saccharification of cellulosic materials.

In conclusion, according to the present invention, the activity of the cellulases remaining in the solid matter in the degradative saccharification liquor, which has never been utilized heretofore, can be re-utilized by 65 to 100 percent by the remarkably simple operation of contacting the cellulases remaining in the solid matter with insoluble cellulose in aqueous solutions and acidic buffer solutions at a temperature ranging from room temperature to 55° C. The application of the method of the present invention to the enzymatic saccharification of cellulosic materials can therefore drastically save the cost of the operations.

The present invention will be more readily understood by the following examples.

EXAMPLE 1

4 g of finely divided Japanese red pine wood flour was added to 100 ml of an acetate buffer solution having a pH value of 4.5, whereto 200 mg of commercially available cellulase originating from *Aspergillus niger* (Cellulosin AC) was added, and the solution was shaken for 24 hours at 40° C. The reaction liquor, in which 40 percent of the wood flour had been decomposed, was centrifugally separated into a liquid portion and 2.4 g of solid matter. 90 mg of cellulase remained in the liquid portion, which was recovered completely by ultrafiltration.

On the other hand, 2.4 g of the solid matter was suspended in 55 ml of an aqueous solution containing 0.8 percent by weight of glucomannan. The suspension was shaken for 2 hours at 28° C., and then centrifuged. 67 mg of cellulase was contained in the obtained aqueous glucomannan solution. The total amount of the recovered cellulase was 157 mg, which was 78.5 percent recovery.

3.4 g of Japanese red pine wood flour was newly added to the recovered solution of Cellulosin AC so that the total amount of the solution was 80 ml, and enzymatic decomposition was effected at 40° C., yielding 16.5 $\mu$mol of glucose per mg of cellulase per hour. Considering that the initial yield was 16.0 $\mu$mol, it was understood that the activity of Cellulosin AC was not decreased even after recovery.

EXAMPLE 2

100 ml of a water-soluble nutritious culture medium, incorporated with an appropriate amount of cellulose powder as carbon source, was charged into a 500-cc flask and sterilized. *Trichoderma viride* QM 414 was inoculated in this medium and cultured for 6 days at 30° C. under aerobic conditions, the pH value of the culture solution being maintained constantly at 5.4.

5 g of finely divided beech wood flour, 20 to 50$\mu$ in particle size, was charged into another 300-cc flask, whereto 50 ml of the above culture solution (containing 120 mg of the enzyme) was added. After 56 percent of the wood flour had been decomposed by the reaction for 48 hours at 42° C., the reaction liquor was centrifugally separated into a liquid portion and a solid matter. 50 mg of the enzyme remained in the liquid portion, from which 42 mg of the enzyme was recovered by ultrafiltration.

On the other hand, 70 ml of a citrate buffer solution containing 4.5 percent by weight of cellobiose having a pH value of 5.0 was added to the solid matter. 50 mg of the enzyme was contained in the cellobiose solution obtained after the shaking for 2 hours at 10° C. followed by centrifuging. The total recovery of the enzyme was 77 percent.

Japanese fir flour was newly added to the recovered enzyme solution to effect enzymatic saccharification. The recovered enzyme showed the activity on the wood flour which was not lower than that shown initially, even when the amount of the decomposed cellobiose was subtracted as blank.

EXAMPLE 3

4 g of finely divided lauan flour was added to 100 ml of an acetate buffer solution having a pH value of 4.0, whereto 200 mg of commercially available cellulase originating from *Trichoderma viride* (Cellulase-Onozuka R-10) was added, and decomposition was effected for 24 hours at 40° C. The reaction liquor in which 40 percent of the wood flour had been decomposed was centrifugally separated into a liquid portion and 2.2 g of a solid matter. 100 mg of cellulase remained in the liquid portion, from which 85 mg of the cellulase was recovered by ultrafiltration.

On the other hand, 50 ml of a tris buffer solution containing 4 percent by weight of ethanol having a pH value of 5.4 was added to 2.2 g of the solid matter. 70 mg of cellulase was recovered after the solution was shaken for 1 hour at 35° C. The total recovery of cellulase was 77.5 percent. No decrease was recognized in the activity of the recovered cellulase.

EXAMPLE 4

Dried newspaper was cut into 3 mm×3 mm regular square pieces. 2 g of the pieces was suspended in 50 ml of water, whereto 100 mg of Cellulase-Onozuka R-10 was added. After the decomposition for 24 hours at 45° C., the reaction liquor was centrifugally separated into a liquid portion and 1.4 g of a solid matter. 35 mg of cellulase remained in the liquid portion.

40 ml of an aqueous solution containing 15 percent by weight of ethylene glycol was added to 1.4 g of the solid matter, obtained in the manner described above. After the solution was shaken for 2 hours at 25° C., an aqueous ethylene glycol solution containing 47 mg of cellulase was recovered. No decrease was recognized in the activity of the recovered cellulase.

EXAMPLE 5

4 g of dried and mashed corn stalk powder was suspended in 100 ml of an acetate buffer solution having a pH value of 5.0, whereto 100 mg of cellulase originating from *Trichoderma viride* (Cellulase-Onozuka R-10) and 50 mg of cellulase originating from Aspergillus niger (Cellulosin AC) were added. After the decomposition for 2 hours at 35° C., the reaction liquor was centrifugally separated into a liquid portion and 3.2 g of a solid matter. 80 mg of cellulase was recovered from the liquid portion.

On the other hand, 50 ml of an acetate buffer solution of a pH value of 5.0 was added to 3.2 g of the solid matter. After the solution was shaken for 2 hours at 28° C., a solution containing 44 mg of cellulase was obtained by centrifuging. The total recovery of the cellulase was 82.7 percent.

When the recovered cellulase solution was decomposed with the addition of finely divided softwood mixture flour, the amount of the decomposed wood flour per unit time was the same as that of the same wood flour decomposed with the initial enzyme mixture.

EXAMPLE 6

4 g of finely divided hardwood mixture flour was added to 100 ml of an acetate buffer solution having a pH value of 3.9, whereto 200 mg of commercially available cellulase originating from *Trichoderma viride* (Cellulase-Onozuka R-10) was added, and decomposition was effected for 48 hours at 40° C. The reaction liquor in which 55 percent of the wood flour had been decomposed was centrifugally separated into a liquid portion and 1.8 g of a solid matter.

1.8 g of this solid matter was added to 55 ml of a citrate buffer solution having a pH-value of 5.4, whereto 2.5 g of Japanese red pine wood flour was newly added for re-reaction at 40° C. The activity of the cellulase in this reaction was 15.5 μmol in terms of the glucose yield per mg of cellulase per hour. The amount of the re-utilized cellulase was 97 percent based on 16.0 μmol of the cellulase obtained in the initial reaction.

EXAMPLE 7

100 ml of a water-soluble nutritious culture medium, incorporated with an appropriate amount of cellulose powder as carbon source, was charged into a 500-cc flask and sterilized. *Trichoderma viride* QM 414 was inoculated in this medium and cultured for 6 days at 30° C. under aerobic conditions, the pH value of the culture solution being maintained constantly at 5.4.

5 g of finely divided beech wood flour, 20 to 50μ in particle size, was charged into another 300-cc flask, whereto 50 ml of the above culture solution (containing 120 mg of the enzyme) was added. After 56 percent of the wood flour had been decomposed by the reaction for 48 hours at 40° C., the reaction liquor was centrifugally separated into a liquid portion and a solid matter. 35 ml of water was added to this solid matter, whereto 1.4 g of dried and mashed rice straw was added, and decomposition was effected for 48 hours at 45° C. 61 percent of the straw flour was decomposed.

EXAMPLE 8

Dried newspaper was cut into 3 mm×3 mm regular square pieces. 2 g of the pieces was suspended in 50 ml of water, whereto 100 mg of Cellulosin AC was added. After the decomposition for 24 hours at 50° C., the reaction liquor was centrifugally separated into a liquid portion and 1.4 g of a solid matter. 1.4 g of this solid matter was suspended in 30 ml of an acetate buffer solution having a pH value of 5.0, whereto 1.2 g of Japanese red pine wood flour was newly added. After the reaction was effected at 40° C., glucose was produced in a yield of 7.5 μmol per mg of cellulase per hour. The re-utilization ratio of the cellulase activity was 67 percent, as the glucose yield by the initial reaction was 11.3 μmol.

EXAMPLE 9

4 g of dried and mashed bagasse powder was suspended in 100 ml of a phosphate buffer solution having a pH value of 7.0, whereto 80 mg of cellulase originating from *Trichoderma viride* (Cellulase-Onozuka R-10) and 120 mg of cellulase originating from Aspergillus niger (Cellulosin AC) were added. After the decomposition for 24 hours at 35° C., the reaction liquor was centrifugally separated. 2.8 g of the separated solid matter was suspended in 50 ml of a citrate buffer solution having a pH value of 5.0 containing 8 percent by weight of ethanol, whereto 2.0 g of North American timber wood flour was added. After the reaction was effected at 48° C., glucose was produced in a yield of 18.1 μmol per mg of cellulase per hour. The activity recovery was 95 percent as the glucose yield by the initial reaction was 19.0 μmol.

What is claimed is:

1. A process for the saccharification of celluloses, comprising degradatively decomposing a cellulosic material by cellulases in the absence of an alcohol to obtain a liquid portion containing saccharides and a solid matter containing cellulases; separating said liquid portion from said solid matter; and degradatively saccharifying additional cellulosic material with the use of said solid matter in an aqueous solution, an aqueous pH-buffered solution or an aqueous pH-buffered solution of polysaccharides or oligosaccharides.

2. A process for the saccharification of celluloses as set forth in claim 1, wherein said polysaccharide is glucomannan, xylan, galactan, galactoglucomannan, or a mixture thereof.

3. A process for the saccharification of celluloses as set forth in claim 1, wherein said oligosaccharide is cellobiose, cellotriose, cellotetraose, cellopentaose, cellohexaose, glucose-containing mannooligosaccharide, or a mixture thereof.

4. A process for the saccharification of celluloses as set forth in claim 1, wherein the concentration of said polysaccharides or oligosaccharides in said aqueous solution, or aqueous pH-buffered solution is within the range of 0.5 to 5 percent by weight.

5. A process for the saccharification of celluloses as set forth in claim 1, wherein the pH value of said aqueous pH-buffered solutions is within the range of 3.0 to 8.0.

6. A process for the saccharification of celluloses as set forth in claim 1, wherein said newly added cellulosic materials are degradatively saccharified by said solid matter at a temperature ranging from room temperature to 55° C.

* * * * *